United States Patent [19]

Goddard et al.

[11] 4,120,693
[45] Oct. 17, 1978

[54] SUBSTITUTED ISOINDOLES

[75] Inventors: Steven Jerome Goddard, West Grove, Pa.; George Levitt, Wilmington, Del.

[73] Assignee: E. I. Du Pont de Nemours and Company, Wilmington, Del.

[21] Appl. No.: 709,820

[22] Filed: Jul. 29, 1976

[51] Int. Cl.² .................... A01N 9/22; C07D 209/34
[52] U.S. Cl. .................... 71/96; 260/326 A; 260/326 N; 260/326 HL; 260/326.1
[58] Field of Search .............. 260/326 HL; 71/96, 95, 71/88

[56] References Cited

U.S. PATENT DOCUMENTS

| B 536,322 | 3/1976 | Goddard | 71/96 |
|---|---|---|---|
| 2,900,243 | 8/1959 | Lewis | 71/95 |
| 3,476,546 | 11/1969 | Roberts et al. | 71/88 |
| 3,878,224 | 4/1975 | Matsui et al. | 260/326 HL |
| 3,940,419 | 2/1976 | Diehl et al. | 71/96 |
| 3,987,056 | 10/1976 | Cobb | 260/326 HL |
| 3,987,057 | 10/1976 | Goddard | 71/96 |

*Primary Examiner*—Glennon H. Hollrah

[57] ABSTRACT

This invention relates to novel compounds of the formulae and their use as herbicides:

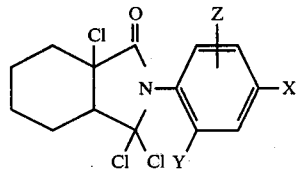

Formula I

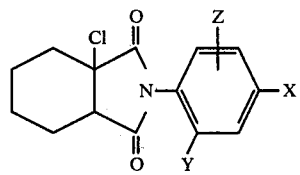

Formula II wherein
X is H, F, Cl, Br, CN, NO₂ or OCH₃;
Y is H, F, or CH₃; and
Z is H, F, Cl, Br or OCH₃ provided that
  (1) when Y is CH₃; X is F, Cl, or Br;
  (2) when Z is 6—Cl or 6—Br, Y is F; and,
  (3) X, Y and Z may not all be H simultaneously.

24 Claims, No Drawings

SUBSTITUTED ISOINDOLES

BACKGROUND OF THE INVENTION

A number of isoindole-type compounds are known in the prior art. Recently, in German Offenlegungsschrift 2,165,651, a group of isoindol-1,3-diones which are useful as herbicides was disclosed. The general formula for the isoindol-1,3-diones is as follows:

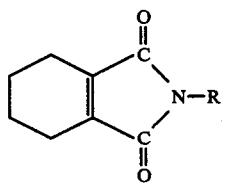

wherein R may be an aryl, aralkyl or benzyl optionally substituted with 1 to 5 halogen atoms; hydroxy, nitro, cyano, thiocyano, carboxy, halogenated alkyl, alkyl, alkoxy, lower alkylthio, phenyl, substituted phenyl or —O—$CH_2$A where A is a phenyl or a naphthyl group, or a phenyl group containing one or more substituent such as halogen, nitro, lower alkyl or lower alkoxy.

Typical of the compounds disclosed in the Offenlegungsschrift is the compound of Structure 1:

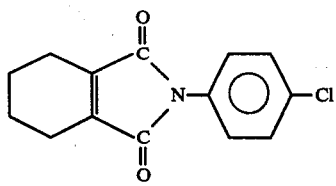

(1)

Although herbicides such as the herbicide discussed above have proven effective in controlling undesired vegetation advancing technology creates constant demand for improved herbicides.

According to the instant invention novel, improved herbicides have been discovered.

DESCRIPTION OF THE INVENTION

This invention relates to novel compounds of the formulae I or II and their use as herbicides for the post-emergence control of undesired vegetation and chemical fallow.

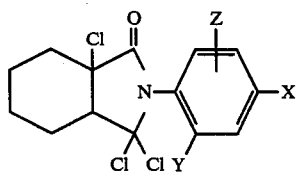

Formula I

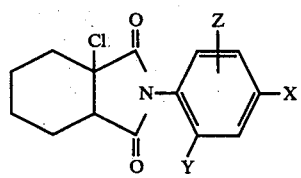

Formula II wherein
X is H, F, Cl, Br, CN, $NO_2$ or $OCH_3$;
Y is H, F or $CH_3$; and
Z is H, F, Cl, Br or $OCH_3$; provided that (1) when Y is $CH_3$, X is F, Cl or Br;
(2) when Z is 6—Cl or 6—Br, Y is F; and,
(3) X, Y and Z may not all be H simultaneously.

Preferred Compounds

Preferred for their high biological activity are those compounds of Formula I or II wherein, independently:
(a) X is F, Cl or Br;
(b) Y is H or F;
(c) Z is H, F, Cl or Br.

More Preferred Compounds

More preferred for their higher biological acivity are compounds of Formula I or II wherein X is Cl or Br, Y is H or F and Z is H.

Specifically Preferred Compounds

Specifically preferred for their outstanding herbicidal activity are:
(a) 3a-chloro-2-(4-chlorophenyl)-3a,4,5,6,7a-hexahydro-1H-isoindole-1,3(2H)-dione, m.p. 116°–117.5° C.
(b) 3a-chloro-2-(4-chloro-2-fluorophenyl)-3a,4,5,6,7,7a-hexahydro-1H-isoindole-1,3(2H)-dione, m.p. 73°–75° C.
(c) 3a-chloro-2-(4-bromo-2-fluorophenyl)-3a,4,5,6,7,7a-hexahydro-1H-isoindole-1,3(2H)-dione, m.p. 81°–82° C.
(d) 3,3,7a-trichloro-2-(4-chloro-2-fluorophenyl)-2,3,3a,4,5,6,7,7a-octahydro-1H-isoindol-1-one, m.p. 145°–147° C.
(e) 3,3,7a-trichloro-2-(4-chloro-2-fluorophenyl)-2,3,3a,4,5,6,7,7a-octahydro-1H-isoindol-1-one, m.p. 161°–163° C.
(f) 3,3,7a-trichloro-2-(4-chlorophenyl)-2,3,3a,4,5,6,7,7a-octahydro-1H-isoindol-1-one, m.p. 123°–125° C.

Synthesis

The compounds of Formulas I and II can be prepared as outlined in the reaction scheme below.

The starting materials for the preferred compounds of this invention, 2-fluoroaniline and 2'-fluoro-acetanilide, can be prepared as described by G. Schiemann and H. G. Baumgarten, Chem. Berichte, 70, 1416 (1937).

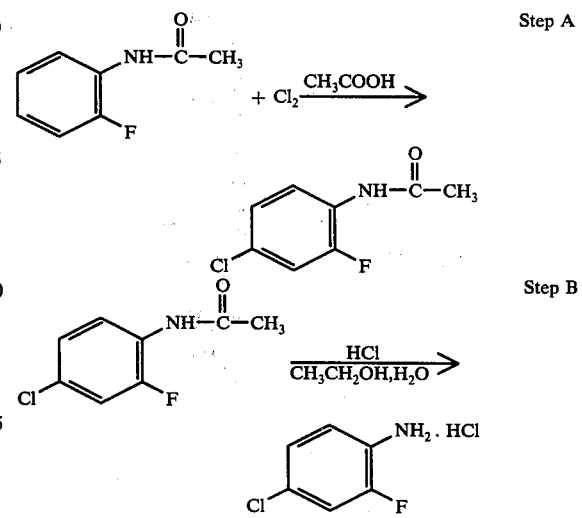

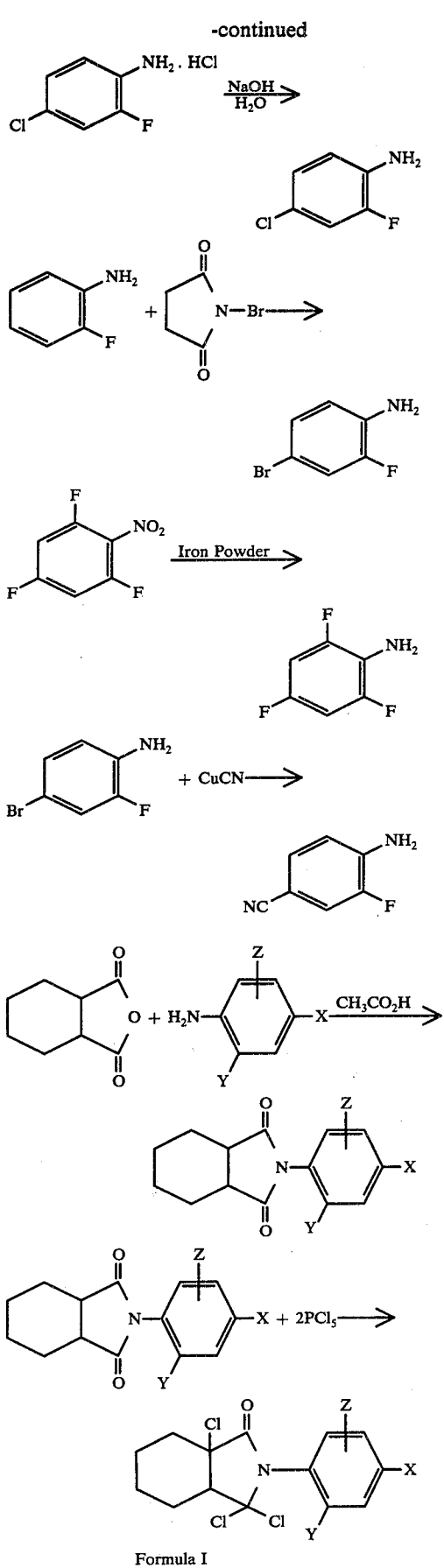

Formula I

Step C

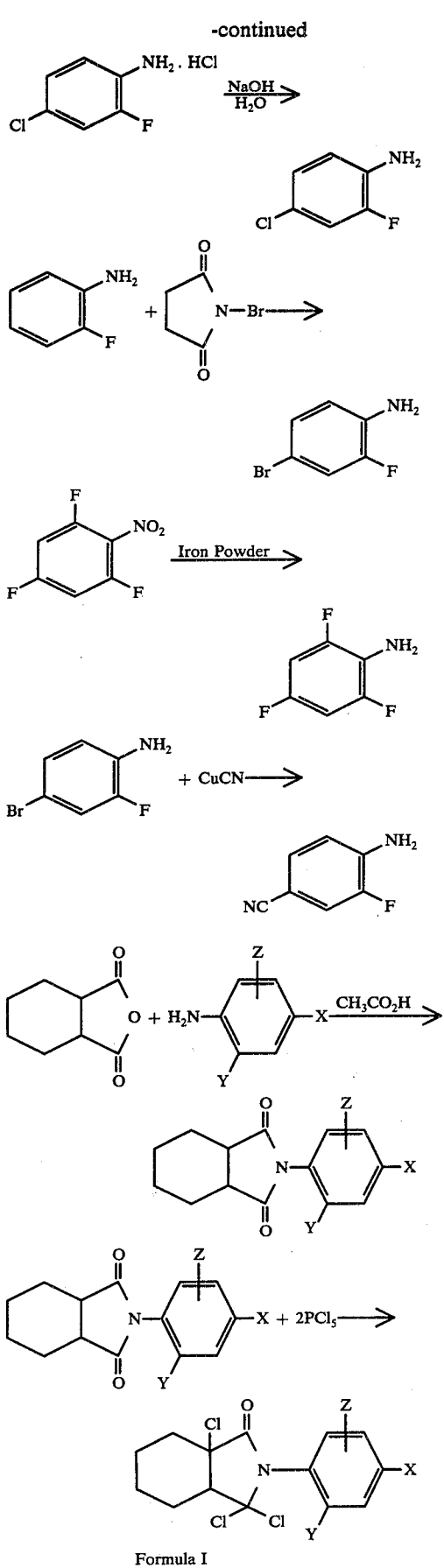

Formula II wherein
X is H, F, Cl, Br, CN, NO₂ or OCH₃
Y is H, F or CH₃ and
Z is H, F, Cl, Br or OCH₃ provided that
(1) when Y is CH₃, X is F, Cl, or Br,
(2) when Z is 6-Cl or 6-Br, Y is F and
(3) X, Y and Z may not all be H simultaneously.

In the explanation below, all temperatures are in degrees centigrade.

Step A

The reaction of 2'-fluoroacetanilide and chlorine in acetic acid is well known to those skilled in the art, e.g., W. W. Reed and K. J. P. Orton, J. Chem. Soc., 91, 1543 (1907) for the chlorination of acetanilide to obtain 2', 4'-dichloroacetanilide. The reaction takes place at 25°–30° over several hours at atmospheric pressure.

Step B

The chlorofluoracetanilide is refluxed in a mixture of a lower alcohol (50%) and concentrated hydrochloric acid (50%) for several hours at 70°–90° and atmospheric pressure. The solvent mixture is removed at a reduced pressure of 100 to 300 mm.Hg and 20°–50° to leave a residue of the hydrochloride salt of 4-chloro-2-fluoroaniline.

Step C

Treatment of an aqueous solution of the hydrochloride salt of 4-chloro-2-fluoraniline with an alkali metal hyroxide solution, yields free 4-chloro-2-fluoroaniline. The free base is extracted into a suitable water-immiscible organic solvent such as ethyl ether or methylene chloride and the crude 4-chloro-2-fluoroaniline is isolated by removal of the organic solvent at a reduced pressure of 100 to 300 mm.Hg at 20°–50°.

Step A'

The reaction of 2-fluoroaniline and N-bromosuccinimide in an inert organic solvent such as methylene chloride is well known to those skilled in the art, e.g., J. B. Wommack et al., J. Het. Chem., 6, 243 (1969). The exothermic reaction takes place at 0° over several hours. The resulting reaction mixture is washed with water several times and dried with an appropriate drying agent such as anhydrous sodium sulfate. The 4-bromo-2-fluoroaniline is recovered by removal of the organic solvent at a reduced pressure of 100 to 300 mm. Hg at 20°–50°.

Step A″

The synthesis of 2,4,6-trifluoroaniline from 1,3,5-trifluoro-2-nitrobenzene uses the same procedure as that described by G. Schiemann and M. Seyhan [Chem. Ber,. 70, 2396 (1937)] for the preparation of 2,4-difluoraniline. The preparation of 1,3,5-trifluoro-2-nitrobenzene is described by V., I. Siele and H. J. Matsuguma, U.S. Dept. Com., Office Serv., P B Rept. 145, 510, p. 1 (1960)[Chem. Abst. 56. 15394C (1962)].

Step A‴

4-Amino-3-fluorobenzonitrile can be prepared from 4-bromo-2-fluoroaniline by treatment with cuprous cyanide in N-methylpyrrolidone using the procedure of L. Friedman, et al. J. Org. Chem, 26, 2522 (1961). The reaction mixture is heated at reflux for several hours and then poured into ice and sodium cyanide. The resulting solution is heated between 50°–80° for a period of 1–3 hours, cooled and extracted with toluene; the toluene extract is washed with water, dried with a suitable drying agent, and evaporated to give the 4-amino-3-fluorobenzonitrile.

2-Fluoro-4-methoxyaniline is known in the art and can be prepared by the method of H. Hodgson, et al., J. Chem. Soc., 1268 (1940).

2-Fluoro-4-nitroaniline is also a known compound and can be prepared according to the method of J. B. Dickey, U.S. Pat. No. 2,436,100.

Step D

The substituted aniline (from Steps C, A′, A″or A‴) and cyclohexane-1,2-dicarboxylic anhydride are refluxed together in glacial acetic acid at temperatures of 115°–120° and atmospheric pressure for several hours (e.g. more than 5). The substituted phenyl-3a,4,5,6,7,7a-hexa-hydro-1H-isoindole-1,3(2H)-dione is isolated by precipitation with water followed by filtration.

Step E

The 2-substituted aryl-3a,4,5,6,7,7a-hexa-hydro-1H-isoindole-1,3(2H)-dione is mixed with two equivalents of solid phosphorous pentachloride and a small amount (1 to 5 parts) of phosphorous oxychloride and the mixture heated to reflux (i.e. 80–140) for several hours (i.e. 2 to 10). Volatile constituents of the mixture are removed at reduced pressure (i.e. 20 to 300 mm.Hg) and the resulting crude product recrystallized from a non-hydroxylic solvent (such as methyl cyclohexane) to isolate the 3,3,7a-trichloro-2-substituted aryl-2,3,3a,4,5,6,7,7a-octahydro-1H-isoindol-1-one.

Step F

The controlled hydrolysis of the 3,3,7a-trichloro-2-substituted aryl-2,3,3a,4,5,6,7,7a-octahydro-1H-isoindol-1-ones to the 3a-chloro-2-aryl-3a,4,5,6,7,7a-hexahydro-1H-isoindole-1,3(2H)-diones is effected by exposure to moist air over an extended period of time, steam, or to water in a non-hydroxylic solvent (such as ether).

The following examples further illustrate the method for synthesis of compounds of this invention. All parts are by weight and all temperatures in degrees centigrade unless otherwise indicated.

Example 1

Preparation of 2-(4-chloro-2-fluorophenyl)-3a,4,5,6,7,7a-hexahydro-1H-isoindole-1,3(2H)-dione Seventy-one parts of liquid chlorine were added to a solution of 140 parts of 2′-fluoroacetanilide in 500 parts glacial acetic acid, during one hour, at 25°–27°, with ice water cooling. While stirring for 4 hours at 25°–27°, 4′-chloro-2′-fluoroacetanilide precipitated. After collecting the product by filtration, the filtrate was poured into 2000 parts of ice. The resulting second portion of precipitated product was collected by filtration, combined with the first portion and recrystallized from 700 parts of methanol at −45° to yield 119 parts of 4′-chloro-2′-fluoroacetanilide as white crystals melting at 152°–155°.

A mixture of 119 parts of 4′-chloro-2′-fluoroacetanilide in 475 parts of ethanol and 200 parts of 37% hydrochloric acid was refluxed for 17 hours and the solvent removed at a reduced pressure of 300 mm.Hg to yield the moist, solid hydrochloride salt of 4-chloro-2-fluoroaniline.

The moist, solid hydrochloride salt of 4-chloro-2-fluoroaniline was cooled to 10° in an ice-acetone bath and 50% aqueous sodium hydroxide was added dropwise, with stirring, until pH 11 was obtained. The resulting two-phase mixture was extracted four times; 500 parts of methylene chloride were used for each extraction. The combined organic extracts were dried with anhyrous sodium sulfate and the solvent removed at a reduced pressure of 300 mm.Hg to leave 89 parts of light brown, oily 4-chloro-2-fluoroaniline, $n_D^{25}$ = 1.5541.

9.44 parts of 4-chloro-2-fluoroaniline were then added to a solution of 10 parts of cyclohexane-1,2-dicarboxylic anhydride in 75 parts of glacial acetic acid. After refluxing for 6 hours, the reaction mixture was poured into 200 parts of ice. The resulting crystals were filtered and recrystallized from 70 parts of methanol at −40° C. to yield 12.4 parts of white crystals of 2-(4-chloro-2-fluorophenyl)-3a,4,5,6,7,7a-hexahydro-1H-isoindole-1,3(2H)dione melting at 94°–95.5°.

Example 2

Preparation of 2-(4-bromo-2-fluorophenyl)-3a,4,5,6,7,7a-hexahydro-1H-isoindole-1,3(2H)-dione 160 Parts of solid N-bromosuccinimide were added in portions over a 2 hour period to a solution of 100 parts of 2-fluoroaniline in 400 parts of methylene chloride cooled to 0°. After stirring for 20 minutes, the dark red mixture was washed four times; 200 parts of cold water were used for each washing. The red organic phase was dried with anhydrous sodium sulfate and evaporated at 300 mm.Hg to yield 164 parts of brown, oily 4-bromo-2-fluoroaniline, $n_D^{25}$: 1.5885.

11.4 Parts of 4-bromo-2-fluoroaniline were added to a solution of 10 parts of cyclohexane-1,2-dicarboxylic anhydride in 100 parts of glacial acetic acid and the mixture was stirred for 2 hours. The mixture was refluxed for 20 hours and then poured onto 200 parts of ice. The resulting purple crystals were filtered and recrystallized from 70 parts of methanol at −40° to yield 7.6 parts of lavender crystals of 2-(4-bromo-2-fluorophenyl)-3a,4,5,6,7,7a-hexahydro-1H-isoindole-1,3(2H)-dione melting at 90°–92°.

EXAMPLE 3

Preparation of
4-(1,3-dioxo-2,3,3a,4,5,6,7,7a-octahydro-1H-isoindol-2-yl)-3-fluorobenzonitrile Preparation of 4-Amino-3-fluorobenzonitrile 6.8 Parts of 4-bromo-2-fluoroaniline were dissolved in 75 parts of N-methylpyrrolidone. This solution was treated with 4.2 parts of cuprous cyanide. The reaction mixture was heated to 190° for 2 hours. The reaction mass was poured into a mixture of 200 parts of ice and 15 parts of sodium cyanide. This mixture was then heated on a steam bath for 2 hours at 60°-70°. This aqueous solution was then extracted with four 100-part portions of toluene. The toluene extracts were combined and washed with four 300-part portions of water followed by 100-parts of saturated aqueous NaCl. The toluene solution of the product was dried over sodium sulfate and evaporated at a reduced pressure of 50 mm.Hg to give 2.6 parts of 4-amino-3-fluorobenzonitrile, m.p. 71°-73°.

To a solution of 5 parts of cis-1,2-cyclohexane dicarboxylic anhydride in 75 parts of glacial acetic acid was added 4.8 parts of 4-amino-3-fluorobenzonitrile in one portion. The mixture was refluxed for 4 hours, poured over 200 parts of ice and filtered. The crude crystalline product was recrystallized from methanol to yield 4.4 parts of beige 4-(1,3-dioxo-2,3,3a,4,5,6,7,7a-octahydro-1H-isoindol-2-yl)-3-fluorobenzonitrile melting 120°-123°.

By replacing 4-amino-3-fluorobenzonitrile with the appropriately substituted aniline in Example 3, the following compounds can be prepared:

2-(2,4-difluorophenyl)-3a,4,5,6,7,7a-hexahydro-1H-isoindole-1,3(2H)-dione, m.p. 117°-123°.
2-(2,4,6-trifluorophenyl)-3a,4,5,6,7,7a-hexahydro-1H-isoindole-1,3(2H)-dione, m.p. 129°-131°.
2-(4-chlorophenyl)-3a,4,5,6,7,7a-hexahydro-1H-isoindole-1,3(2H)-dione, m.p. 156°-158°.
2-(2-fluoro-4-methoxyphenyl)-3a,4,5,6,7,7a-hexahydro-1H-isoindole-1,3(2H)-dione.
2-(4-bromophenyl)-3a,4,5,6,7,7a-hexahydro-1H-isoindole-1,3(2H)-dione, m.p. 172.5°-173.5°.
2-(4-chloro-2,5-difluorophenyl)-3a,4,5,6,7,7a-hexahydro-1H-isoindole-1,3(2H)-dione, m.p. 87°-88°.
2-(4-chloro-2,6-difluorophenyl)-3a,4,5,6,7,7a-hexahydro-1H-isoindole-1,3(2H)-dione, m.p. 132°-135°.
2-(4-fluorophenyl)-3a,4,5,6,7,7a-hexahydro-1H-isoindole-1,3(2H)-dione.
2-(2-fluoro-4-nitrophenyl)-3a,4,5,6,7,7a-hexahydro-1H-isoindole-1,3(2H)-dione.
2-(2,4-dichloro-5-methoxyphenyl)-3a,4,5,6,7,7a-hexahydro-1H-isoindole-1,3(2H)-dione.
2-(4-nitrophenyl)-3a,4,5,6,7,7a-hexahydro-1H-isoindole-1,3(2H)-dione.
2-(4-methoxyphenyl)-3a,4,5,6,7,7a-hexahydro-1H-isoindole-1,3(2H)-dione.
2-(4-chloro-2-methylphenyl)-3a,4,5,6,7,7a-hexahydro-1H-isoindole-1,3(2H)-dione.
2-(2-fluorophenyl)-3a,4,5,6,7,7a-hexahydro-1H-isoindole-1,3(2H)-dione.
2-(2,4-dichlorophenyl)-3a,4,5,6,7,7a-hexahydro-1H-isoindole-1,3(2H)-dione.
4-(1,3-dioxo-2,3,3a,4,5,6,7,7a-octahydro-1H-isoindol-2-yl)-benzonitrile.
2-(2-fluoro-4,5-dichlorophenyl)-3a,4,5,6,7,7a-hexahydro-1H-isoindole-1,3(2H)-dione.
2-(2-fluoro-4,5-dibromophenyl)-3a,4,5,6,7,7a-hexahydro-1H-isoindol-1,3(2H)-dione.

EXAMPLE 4

Preparation of 3,3,7a-trichloro-2-(4-chlorophenyl)-2,3,3a,4,5,6,7,7a-octahydro-1H-isoindol-1-one An intimate mixture of 20 parts of 2-(4-chlorophenyl)-3a,4,5,6,7,7a-hexahydro-1H-isoindole-1,3(2H)-dione, 35 parts of granular phosphorous pentachloride and 3 parts of phosphorous oxychloride was heated gently until liquification occurred then refluxed for 2 hours. The volatile components were removed by evaporation at 50 mm. Hg and 50° to give 22.4 parts of a grey oil. The oil was crystallized from 100 parts of methylcyclohexane at −40° to yield 21.8 parts of grey, crystalline 3,3,7a-trichloro-2-(4-chlorophenyl)-2,3,3a,4,5,6,7,7a-octahydro-1H-isoindol-1-one m.p. 120°-123.5°. After two recrystallizations from methylcyclohexane an analytic sample was obtained, m.p. 123°-125°.

EXAMPLE 5

Preparation of
3,3,7a-trichloro-2-(4-bromophenyl)-2,3,3a,4,5,6,7,7a-octahydro-1H-isoindol-1-one An intimate mixture of 40 parts of 2-(4-bromophenyl)-3a,4,5,6,7,7a-hexahydro-1H-isoindole-1,3(2H)-dione and 60 parts of granular phosphorous pentachloride was heated gently until liquification occurred. The mixture was then heated to reflux (104°-105°) for 5 hours and evaporated at 50 mm.Hg at 50° to an oil which was diluted with 100 parts of toluene and cooled to −40°. The resulting crystals were filtered to yield 20.2 parts of off-white 3,3,7a-trichloro-2-(4-bromophenyl)-2,3,3a,4,5,6,7,7a-octahydro-1H-isoindol-1-one melting at 148°-150°.

By replacing 2-(4-bromophenyl)-3a,4,5,6,7,7a-hexahydro-1H-isoindole-1,3(2H)-dione in Example 5 with the appropriate 2-substituted aryl-3a,4,5,6,7,7a-hexahydro-1H-isoindole-1,3(2H)-dione, the following compounds can be prepared:

3,3,7a-trichloro-2-(4-chloro-2-fluorophenyl)-2,3,3a,4,5,6,7,7a-octahydro-1H-isoindol-1-one, m.p. 145°-147°.
3,3,7a-trichloro-2-(4-bromo-2-fluorophenyl)-2,3,3a,4,5,6,7,7a-octahydro-1H-isoindol-1-one, m.p. 161.0°-163.5°.
3,3,7a-trichloro-2-(2,4-difluorophenyl)-2,3,3a,4,5,6,7,7a-octahydro-1H-isoindol-1-one.
3,3,7a-trichloro-2-(2,4,6-trifluorophenyl)-2,3,3a,4,5,6,7,7a-octahydro-1H-isoindol-1-one.
3,3,7a-trichloro-2-(2-fluoro-4-methoxyphenyl)-2,3,3a,4,5,6,7,7a-octahydro-1H-isoindol-1-one.
3,3,7a-trichloro-2-(B 4-chloro-2,5-difluorophenyl)-2,3,3a,4,5,6,7,7a-octahydro-1H-isoindol-1-one.
3,3,7a-trichloro-2-(4-chloro-2,6-difluorophenyl)-2,3,3a,4,5,6,7,7a-octahydro-1H-isoindol-1-one.
3,3,7a-trichloro-2-(2-fluoro-4-nitrophenyl)-2,3,3a,4,5,6,7,7a-octahydro-1H-isoindol-1-one.
3,3,7a-trichloro-2-(2,4-dichloro-5-methoxyphenyl)-2,3,3a,4,5,6,7,7a-octahydro-1H-isoindol-1-one.
3,3,7a-trichloro-2-(4-nitrophenyl)-2,3,3a,4,5,6,7,7a-octahydro-1H-isoindol-1-one.
3,3,7a-trichloro-2-(4-methoxyphenyl)-2,3,3a,4,5,6,7,7a-octahydro-1H-isoindol-1-one.
3,3,7a-trichloro-2-(4-chloro-2-methylphenyl)-2,3,3a,4,5,6,7,7a-octahydro-1H-isoindol-1-one.

3,3,7a-trichloro-2-(2-fluorophenyl)-2,3,3a,4,5,6,7,7a-octahydro-1H-isoindol-1-one.
3,3,7a-trichloro-2-(2,4-dichlorophenyl)-2,3,3a,4,5,6,7,7a-octahydro-1H-isoindol-1-one.
3,3,7a-trichloro-2-(4-fluorophenyl)-2,3,3a,4,5,6,7,7a-octohydro-1H-isoindol-1-one.
3-fluoro-4-(1,1,3a-trichloro-2,3,3a,4,5,6,7,7a-octahydro-3-oxo-1H-isoindol-2-yl)benzonitrile.
4-(1,1,3a-trichloro-2,3,3a,4,5,6,7,7a-octahydro-3-oxo-1H-isoindol-2-yl)benzonitrile.
3,3,7a-trichloro-(2-(2-fluoro-4,5-dichlorophenyl)-2,3,3a,4,5,6,7,7a-octahydro-1H-isoindol-1-one.
3,3,7a-trichloro-2-(2-fluoro-4,5-dibromophenyl)-2,3,3a,4,5,6,7,7a-octahydro-1H-isoindol-1-one.

EXAMPLE 6

Preparation of
3a-chloro-2-(4-chlorophenyl)-3a,4,5,6,7,7a-hexahydro-1H-isoindole-1,3(2H)-dione An intimate mixture of 20 parts of 2(4-chlorophenyl)-3a,4,5,6,7,7a-hexahydro-1H-isoindol-1,3(2H)-dione, 35 parts of granular phosphorous pentachloride and 5 parts of phosphorous oxychloride was heated to reflux during 2 hours and then refluxed for 28 hours. The volatile components were removed by evaporation at 50° and 50 mm. Hg to yield a dark oil. The oil was crystallized from acetonitrile to yield 13 parts of flake off-white crystals melting at 79°–82°. After standing for an extended period of time occasionally exposed to ambient humidity, an aliquat of the crystals was recrystallized 3 times from methyl cyclohexane to yield 3a-chloro-2-(4-chlorophenyl)-3a,4,5,6,7,7a-hexahydro-1H-isoindole-1,3(2H)-dione melting at 116°–117.5°. Mass spectrum shows a parent ion of 297.

EXAMPLE 7

Preparation of
3a-Chloro-2-(4-bromo-2-fluorophenyl)-3a,4,5,6,7,7a-hexahydro-1H-isoindole-1,3(2H)-dione.

5 parts of 3,3,7a-trichloro-2-(4-bromo-2-fluorophenyl)-2,3,3a,4,5,6,7,7a-octahydro-1H-isoindol-1-one was exposed to steam for 90 minutes. The resulting gum was dissolved in 100 parts of chloroform and dried with anhydrous sodium sulfate. The solution was evaporated at 50 mm.Hg at 50° to yield a glass which was crystallized from 15 parts of methylcyclohexane to yield 2.8 parts of 3a-chloro-2-(4-bromo-2-fluorophenyl)-3a,4,5,6,7,7a-hexahydro-H-isoindole-1,3(2H)-dione melting 81°–82°.

EXAMPLE 8

Preparation of
3a-chloro-2-(4-chloro-2-fluorophenyl)-3a,4,5,6,7,7a-hexahydro-1H-isoindole-1,3(2H)-dione A solution of one part of 3,3,7a-trichloro-2-(4-chloro-2-fluorophenyl)-2,3,3a,4,5,6,7,7a-octahydro-1H-isoindol-1-one in 200 parts of diethylether was added to 5 parts of water. After stirring for 24 hours at reflux, the solvent and resultant hydrogen chloride are removed at ambient temperature and 300 mm.Hg to yield a solid. The solid is recrystallized from methylcyclohexane a yield 3a-chloro-2-(4-chloro-2-fluorophenyl)-3a,4,5,6,7,7a-hexahydro-1H-isoindole-1,3(2H)-dione, m.p. 73°–75°.

By replacing 3,3,7a-trichloro-2-(4-chloro-2-fluorophenyl)-2,3,3a,4,5,6,7,7a-octahydro-1H-isoindol-1-one in Example 8 with the appropriately substituted 3,3,7a-trichloro-2-aryl-2,3,3a,4,5,6,7,7a-octahydro-1H-isoindol-1-one the following compounds can be made:

3a-chloro-2-(4-bromophenyl)-3a,4,5,6,7,7a-hexahydro-1H-isoindol-1,3(2H)-dione
3a-chloro-2-(2,4-difluorophenyl)-3a,4,5,6,7,7a-hexahydro-1H-isoindol-1,3(2H)-dione
3a-chloro-2(2,4,6-trifluorophenyl)-3a,4,5,6,7,7a-hexahydro-1H-isoindol-1,3(2H)-dione
3a-chloro-2-(2-fluoro-4-methoxyphenyl)-3a,4,5,6,7,7a-hexahydro-1H-isoindol-1,3(2H)-dione
3a-chloro-2-(4-chloro-2,5-difluorophenyl)-3a,4,5,6,7,7a-hexahydro-1H-isoindol-1,3(2H)-dione
3a-chloro-2-(4-chloro-2,6-difluorophenyl)-3a,4,5,6,7,7a-hexahydro-1H-isoindol-1,3(2H)-dione
3a-chloro-2-(2-fluoro-4-nitrophenyl)-3a,4,5,6,7,7a-hexahydro-1H-isoindol-1,3(2H)-dione
3a-chloro-2-(2,4-dichloro-5-methoxyphenyl)-3a,4,5,6,7,7a-hexahydro-1H-isoindol-1,3(2H)-dione
3a-chloro-2-(4-nitrophenyl)-3a,4,5,6,7,7a-hexahydro-1H-isoindol-1,3(2H)-dione
3a-chloro-2-(4-methoxyphenyl)-3a,4,5,6,7,7a-hexahydro-1H-isoindol-1,3(2H)-dione p1 3a-chloro-2-(4-chloro-2-methylphenyl)-3a,4,5,6,7,7a-hexahydro-1H-isoindol-1,3(2H)-dione
3a-chloro-2-(2-fluorophenyl)-3a,4,5,6,7,7a-hexahydro-1H-isoindol-1,3(2H)-dione
3a-chloro-2-(2,4-dichlorophenyl)-3a,4,5,6,7,7a-hexahydro-1H-isoindol-1,3(2H)-dione
3a-chloro-2-(4-fluorophenyl)-3a,4,5,6,7,7a-hexahydro-1H-isoindol-1,3(2H)-dione
4-(3a-chloro-2,3,3a,4,5,6,7,7a-octahydro-1,3-dioxo-1H-isoindol-2-yl)-3-fluorobenzonitrile
4-(3a-chloro-2,3,3a,4,5,6,7,7a-octahydro-1,3-dioxo-1H-isoindol-2-yl)-benzonitrile
3a-chloro-2-(2-fluoro-4,5-dichlorophenyl)-3a,4,5,6,7,7a-hexahydro-1H-isoindol-1,3(2H)-dione
3a-chloro-2-(2-fluoro-4,5-dibromophenyl)-3a,4,5,6,7,7a-hexahydro-1H-isoindol-1,3(2H)-dione Formulations Useful formulations of the compounds of Formulae I and II can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few pints to several hundred gallons per acre. High strength compositions are primarily used as intermediates for further formulation. The formulations, broadly, contain about 1% to 99% by weight of active ingredient(s) and at least one of a) about 0.1% to 20% surfactant(s) and b) about 5% to 99% solid or liquid diluent(s). More specifically, they will contain these ingredients in the following approximate proportions:

| | Percent by Weight | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions (including Emulsifiable Concentrates) | 5–50 | 40–95 | 0–15 |
| Aqueous Suspensions | 10–50 | 40–84 | 1–20 |

-continued

| | Percent by Weight | | |
|---|---|---|---|
| | Active Ingredient | Diluent(s) | Surfactant(s) |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers," 2nd Edn., Dorland Books, Caldwell, N.J. The more absorptive diluents are preferred for wettable powders and the denser ones for dusts. Typical liquid diluents and solvents are described in Marsden, "Solvents Guide," 2nd Edn., Interscience, New York, 1950. Solubility under 0.1% is preferred for suspension concentrates; solution concentrates are preferable stable against phase separation at 0° C. "McCutcheon's Detergents and Emulsifiers Annual," Allured Publ. Corp., Ridgewood, New Jersey, as well as Sisely and Wood, "Encyclopedia of Surface Active Agents," Chemical Publ. Co., Inc. New York, 1964, list surfactants and recommended uses. All formulations can contain minor amounts of additives to reduce foam, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration," Chemical Engineering, Dec. 4, 1967, pp. 147ff. and "Perry's Chemical Engineer's Handbook," 4th Ed., McGraw-Hill, N.Y., 1963, pp. 8-59ff.

For further information regarding the art of formulation, see for example:

H. M. Loux, U.S. Patent 3,235,361, February 15, 1966, Col. 6, Line 16 through Col. 7, Line 19 and Examples 10 through 41.

R. W. Luckenbaugh, U.S. Patent 3,309,192, March 14, 1967, Col. 5, Line 43 through Col. 7, Line 62 and Examples 8, 12, 15, 39, 41, 52, 53, 58, 132, 138-140, 162-164, 166, 167, 169-182.

H. Gysin and E. Knusli, U.S. Patent 2,891,855, June 23, 1959, Col. 3, Line 66 through Col. 5 Line 17 and Examples 1-4.

G. C. Klingman, "Weed Control as a Science", John Wiley & Sons, Inc., New York, 1961 pp. 81-96.

J. D. Fryer and S. A. Evans, "Weed Control Handbook", 5th Edn., Blackwell Scientific Publications, Oxford, 1968, pp. 101-103.

EXAMPLE 9

| Wettable Powder | |
|---|---|
| 3a-chloro-2-(2-fluoro-4-chlorophenyl)-3a,4,5,6,7,7a-hexahydro-1H-isoindole-1,3(2H)-dione | 80% |
| sodium alkylnaphthalenesulfonate | 2% |
| sodium ligninsulfonate | 2% |
| synthetic amorphous silica | 3% |
| kaolinite | 13% |

The materials are blended then passed through a hammermill to produce particles essentially all below 50 microns in size and then reblended.

EXAMPLE 10

| Wettable Powder | |
|---|---|
| 3a-chloro-2-(4-chlorophenyl)-3a,4,5,6,7,7a-hexahydro-1H-isoindole-1,3(2H)-dione | 40% |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended, passed through an air mill, to produce an average particle size under 15 microns, reblended, and sifted through a U.S.S. No. 50 sieve (0.3 mm. opening) before packaging.

All compounds of the invention may be formulated in the same manner.

EXAMPLE 11

| Granule | |
|---|---|
| wettable powder of Example 10 | 15% |
| gypsum | 69% |
| potassium sulfate | 16% |

The ingredients are blended in a rotating mixer and water sprayed on to accomplish granulation. When most of the material has reached the desired range of 1.0 to 0.42 mm. (U.S.S. 18 to 40 sieves), the granules are removed, dried, and screened. Oversize material is crushed to produce additional material in the desired range. These granules contain 6% active ingredient.

EXAMPLE 12

| Oil Suspension | |
|---|---|
| 3a-chloro-2-(2-fluoro-4-chlorophenyl)-3a,4,5,6,7,7a-hexahydro-1H-isoindole-1,3(2H)-dione | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 13

| Solution | |
|---|---|
| 3a-chloro-2-(2-fluoro-4-bromophenyl)-3a,4,5,6,7,7a-hexahydro-1H-isoindol-1,3(2H)-dione | 30% |
| dimethylformamide | 70% |

Utility

The compounds of the present invention are useful when applied as foliar treatments for broad-spectrum control of undesirable weed and brush species at industrial sites, along railroad and utility rights-of-way, on storage lots, along fences, etc. The compounds also are well adapted to chemical fallow treatments in semi-arid regions and for weed control in "no-till" crop production systems.

The precise amount of the compounds of the invention to be used in any given situation will vary according to the particular end result desired, the use involved, the plant species to be controlled, the formulation used, the mode of application, prevailing weather conditions, foliage density and like factors. The numerous variables preclude giving a rate of application suitable for all situations. Broadly speaking, the compounds of the invention are used at levels of about 0.25 to about 10 kg/ha, preferably about 0.5 to about 5 kg/ha.

Herbicidal activity of the subject compounds was discovered in greenhouse tests.

In the following Test A seeds of crabgrass (*Digitaria spp.*), barnyard grass (*Echinochloa crusgalli*), wild oats (*Avena fatua*), *Cassis tora*, morning glory (*Ipomoea spp.*), cocklebur (*Xanthium spp.*), sorghum, corn, soybean, rice, wheat and nutsedge tubers were planted in a growth medium and treated preemergence with the chemicals dissolved in a non-phytotoxic solvent. At the same time, cotton having five leaves (including cotyledonary ones), bush beans with the third trifoliate leaf expanding, crabgrass with two leaves, barnyard grass with two leaves, wild oats with one leaf, cassia with three leaves (including cotyledonary ones), morning glory with four leaves (including the cotyledonary ones), cocklebur with four leaves (including the cotyledonary ones), sorghum with three leaves, corn with three leaves, soybean with two cotyledonary leaves, rice with two leaves, wheat with one leaf, and nutsedge with three-five leaves were sprayed. Treated plants and controls were maintained in a greenhouse for sixteen days, whereupon all species were compared to controls and visually rated for response to treatment. Ratings are based on a numerical scale extending from 0 = no injury, to 10 = complete kill. The accompanying descriptive symbols have the following meanings: B = burn; G = growth retardation, C = chlorosis/necrosis; E = emergence inhibition; and H = formative effects. The ratings for the compounds tested by this procedure are shown in the table for test A.

TEST A

POST EMERGENCE

| COMPOUND | LB. PER ACRE | BUSH BEAN | COTTON | MORNING GLORY | COCKLEBUR | CASSIA | NUT-SEDGE | CRAB-GRASS | BARN-YARD GRASS | WILD OATS | WHEAT | CORN | SOYBEAN | RICE | SORGHUM |
|---|---|---|---|---|---|---|---|---|---|---|---|---|---|---|---|
| 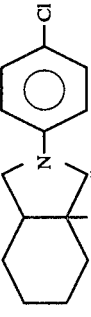 | 2 | 8B | 8B | 10B | 6B | 4B | 3B | 10B | 10B | 10B | 7B | 8B | 9B | 9B | 10B |
|  | 0.4 | 10B | 9B | 10B | 9B | 9B | 9B | 10B | 10B | 9B | 7B | 8B | 8B | 10B | 10B |
| 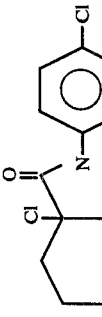 | 0.4 | 10B | 9B | 9B | 9B | 8B | 4B | 9B | 10B | 7B | 5B | 7B | 8B 5X | 9B | 9B |
| 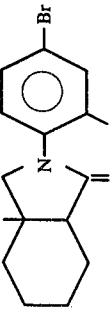 | 0.4 | 10B | 9B | 9B | 10B | 10B | 6B | 8B | 10B | 9B | 7B | 8B | 8B | 10B | 10B |
|  | 0.4 | 10B | 9B | 10B | 10B | 10B | 7B | 8B | 10B | 8B | 7B | 9B | 10B | 9B | 10B |

PRE-EMERGENCE

| COMPOUND | LB. PER ACRE | MORNING GLORY | COCKLEBUR | CASSIA | NUT-SEDGE | CRAB-GRASS | BARN-YARD GRASS | WILD OATS | WHEAT | CORN | SOYBEAN | RICE | SORGHUM |
|---|---|---|---|---|---|---|---|---|---|---|---|---|---|

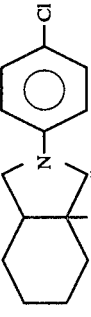
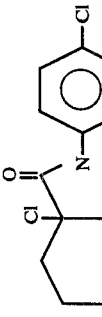
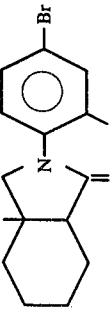

TEST A-continued
| | | | | | | | | | | | | | | | |
|---|---|---|---|---|---|---|---|---|---|---|---|---|---|---|---|
| 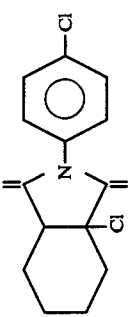 | 2 | 2G | 0 | 2C | 0 | 10E | 10C | 10C | 6C | 1H | 1H | 8C | 8C | | |
| 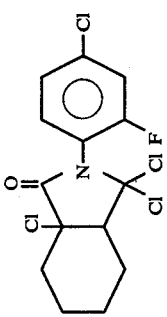 | 0.4 | 1C 9H | 0 | 0 | 0 | 2H | 1C 5H | 1C | 2C | 1C 5G | 5G | 2C | 1C 8G | | |
| 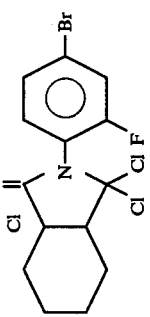 | 0.4 | 0 | 0 | 0 | 0 | 10E | 2C 8G | 2G | 2C 4G | 3H | 0 | 1C | 1C 7G | | |
| 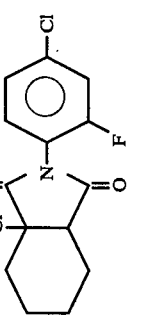 | 0.4 | 1C | 1C | 1C | 1C | 0 | 5C | 2C | 4C | 1C 5G | 2H | 5C | 1C 8G | | |
| 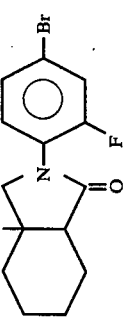 | 0.4 | 2C | 1C | 2C | 1C | 1C | 1C 7G | 2C | 7C | 1C 4G | 3G | 7C | 9C | | |

In test B, plastic pots filled with Fallsington sandy loam were planted to soybeans, cotton, alfalfa, corn, rice, wheat, sorghum, velvetleaf (*Abutilon theophrasti*), sesbania (*Sesbania exaltata*), cassia (Cassia tora), morning glory (*Ipomoea spp.*) jimsonweed (*Datura stramonium*), cocklebur (*Xanthium pensylvanicum*), crabgrass (*Digitaria spp.*), nutsedge (*Cyperus rotundus*), barnyard grass (*Echinochloa crusgalli*), giant foxtail (*Setaria faberi*) and wild oats (*Avena fatua*). Eighteen days after planting, the young plants and the soil around them were sprayed overall with the test chemicals dissolved in a nonphytotoxic solvent. Fourteen days after treatment, all species were compared to untreated controls and visually rated for response to treatment. The ratings are based on a numerical scale extending from 0 = no injury, to 10 = complete kill. The accompanying descriptive symbols have the following meanings: B = burn; and C = chlorosis/necrosis. The ratings for the compounds tested by this procedure are presented in the table for test B.

Test B

| COMPOUND | Rate, kg/ha | Soy-beans | Velvet-leaf | Ses-bania | Cassia | Cotton | Morning glory | Alfalfa | Jimson-weed | Cockle-bur | Corn | Crab-grass | Rice | Nut-sedge | Barn-yard grass | Wheat | Giant Foxtail | Wild Oats | Sor-ghum |
|---|---|---|---|---|---|---|---|---|---|---|---|---|---|---|---|---|---|---|---|
| [structure: 4-Cl phenyl, cyclohexane dione with Cl] | 0.125 | 3B | 0 | 0 | 0 | 2B | 3B | 2B | 2B | 2B | 2B | 0 | 0 | 0 | 0 | 0 | 0 | 0 | 2B |
| | 0.5 | 3B | 10B | 7B | 2B | 2B | 4B | 5B | 10B | 4B | 2B | 0 | 2C | 0 | 3B | 3C | 0 | 0 | 3B |
| [structure: 4-Cl phenyl, cyclohexane with Cl, ClF group] | 0.06 | 4B | 10B | 7B | 0 | 6B | 5B | 3B | 10B | — | 2B | 3B | 0 | 2B | 2B | 3B | 3B | 3B | 3B |
| | 0.12 | 3B | 10B | 8B | 0 | 8B | 3B | 4B | 10B | 3B | 2B | 3B | 0 | 1B | 3B | 3B | 4B | 3B | 3B |
| | 0.25 | 5B | 10B | 7B | 2F | 8B | 5B | 5B | 10B | 4B | 3B | 4B | 3B | 2B | 4B | 4B | 6B | 3B | 4B |
| [structure: 4-Br, 2-F phenyl, cyclohexane with Cl, ClF group] | 0.125 | 2B | 0 | 3B | 2B | 6B | 5B | 2B | 10B | 2B | 1B | 2B | 2B | 2B | 3B | 3B | 3B | 2B | 2B |
| | 0.5 | 4B | 10B | 4B | 6B | 10B | 8B | 9B | 10B | 6B | 2B | 4B | 7B | 3B | 6B | 6B | 5B | 5B | 6B |

What is claimed is:

1. A compound of the formulae

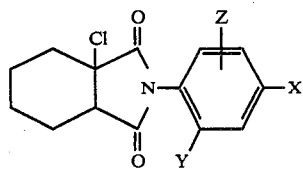

wherein X is H, F, Cl, Br, CN, $NO_2$ or $OCH_3$; Y is H, F or $CH_3$; and Z is H, F, Cl, Br or $OCH_3$ provided that
(1) when Y is $CH_3$, X is F, Cl or Br;
(2) when Z is 6-Cl or 6-Br, Y is F; and,
(3) X, Y and Z may not all be H simultaneously.

2. A compound of claim 1 wherein X is F, Cl or Br.
3. A compound of claim 1 wherein Y is H or F.
4. A compound of claim 1 wherein Z is H, F, Cl or Br.
5. A compound of claim 1 wherein X is Cl or Br, Y is H or F and Z is H.
6. The compound of claim 1, 3a-chloro-2-(4-chlorophenyl)-3a,4,5,6,7,7a-hexahydro-1H-isoindole-1,3(2H)-dione.
7. A compound of claim 1, 3a-chloro-2-(4-chloro-2-fluorophenyl)-3a,4,5,6,7,7a-hexahydro-1H-isoindole-1,3(2H)-dione.
8. The compound of claim 1, 3a-chloro-2-(4-bromo-2-fluorophenyl)-3a,4,5,6,7,7a-hexahydro-1H-isoindole-1,3(2H)-dione.
9. A composition for the control of undesirable vegetation consisting essentially of an effective amount of a compound of claim 1 and at least one of (a) a surface-active agent and (b) an inert solid or liquid diluent.
10. A composition for the control of undesirable vegetation consisting essentially of an effective amount of a compound of claim 2, and at least one of (a) a surface-active agent and (b) an inert solid or liquid diluent.
11. A composition for the control of undesirable vegetation consisting essentially of an effective amount of a compound of claim 3, and at least one of (a) a surface-active agent and (b) an inert solid or liquid diluent.
12. A composition for the control of undesirable vegetation consisting essentially of an effective amount of a compound of claim 4, and at least one of (a) a surface-active agent and (b) an inert solid or liquid diluent.
13. A composition for the control of undesirable vegetation consisting essentially of an effective amount of a compound of claim 5, and at least one of (a) a surface-active agent and (b) an inert solid or liquid diluent.
14. A composition for the control of undesirable vegetation consisting essentially of an effective amount of the compound of claim 6, and at least one of (a) a surface-active agent and (b) an inert solid or liquid diluent.
15. A composition for the control of undesirable vegetation consisting essentially of an effective amount of the compound of claim 7, and at least one of (a) a surface-active agent and (b) an inert solid or liquid diluent.
16. A composition for the control of undesirable vegetation consisting essentially of an effective amount of the compound of claim 8, and at least one of (a) a surface-active agent and (b) an inert solid or liquid diluent.
17. A method for the control of undesirable vegetation comprising applying to the locus of such undesired vegetation a herbicidally effective amount of a compound of claim 1.
18. A method for the control of undesirable vegetation comprising applying to the locus of such undesirable vegetation a herbicidally effective amount of a compound of claim 2.
19. A method for the control of undesirable vegetation comprising applying to the locus of such undesirable vegetation a herbicidally effective amount of a compound of claim 3.
20. A method for the control of undesirable vegetation comprising applying to the locus of such undesirable vegetation a herbicidally effective amount of a compound of claim 4.
21. A method for the control of undesirable vegetation comprising applying to the locus of such undesirable vegetation a herbicidally effective amount of a compound of claim 5.
22. A method for the control of undesirable vegetation comprising applying to the locus of such undesirable vegetation a herbicidally effective amount of the compound of claim 6.
23. A method for the control of undesirable vegetation comprising applying to the locus of such undesirable vegetation a herbicidally effective amount of the compound of claim 7.
24. A method for the control of undesirable vegetation comprising applying to the locus of such undesirable vegetation a herbicidally effective amount of the compound of claim 8.

* * * * *